US010858398B2

(12) United States Patent
Hartmann et al.

(10) Patent No.: US 10,858,398 B2
(45) Date of Patent: Dec. 8, 2020

(54) LYTIC PEPTIDE BIOSENSOR AND METHODS OF MAKING AND USING THE SAME

(71) Applicant: Deetex, LLC, Boca Raton, FL (US)

(72) Inventors: James Hartmann, Boca Raton, FL (US); Ryan Landis, Boca Raton, FL (US); Michelle Ryan, Lighthouse Point, FL (US); Yousseff Mottii, Boca Raton, FL (US)

(73) Assignee: Deetex, LLC, Boca Raton, FL (US)

( * ) Notice: Subject to any disclaimer, the term of this patent is extended or adjusted under 35 U.S.C. 154(b) by 31 days.

(21) Appl. No.: 16/372,707

(22) Filed: Apr. 2, 2019

(65) Prior Publication Data

US 2019/0300930 A1  Oct. 3, 2019

Related U.S. Application Data

(63) Continuation of application No. 16/368,808, filed on Mar. 28, 2019, now abandoned.

(60) Provisional application No. 62/650,011, filed on Mar. 29, 2018.

(51) Int. Cl.
| | | |
|---|---|---|
| C12Q 1/34 | (2006.01) | |
| C07K 7/08 | (2006.01) | |
| C12Q 1/18 | (2006.01) | |
| C12Q 1/04 | (2006.01) | |
| G01N 33/52 | (2006.01) | |

(52) U.S. Cl.
CPC ............ *C07K 7/08* (2013.01); *C12Q 1/04* (2013.01); *C12Q 1/18* (2013.01); *C12Q 1/34* (2013.01); *G01N 33/52* (2013.01); *G01N 2800/104* (2013.01); *G01N 2800/122* (2013.01); *G01N 2800/205* (2013.01); *G01N 2800/52* (2013.01)

(58) Field of Classification Search
CPC ............ C12Q 1/04; C12Q 1/18; G01N 33/52
See application file for complete search history.

(56) References Cited

U.S. PATENT DOCUMENTS

| | | | |
|---|---|---|---|
| 4,070,247 A | 1/1978 | Burt | |
| 4,608,339 A | 8/1986 | Yoakum et al. | |
| 4,774,173 A * | 9/1988 | Reinhartz | C12Q 1/025 435/29 |
| 5,593,875 A | 1/1997 | Wurm et al. | |
| 5,734,014 A | 3/1998 | Ishima et al. | |
| 6,171,862 B1 | 1/2001 | Abe et al. | |
| 6,200,598 B1 | 3/2001 | Needham | |
| 6,284,484 B1 | 9/2001 | Kopetzki et al. | |
| 6,637,720 B2 | 10/2003 | Brehm et al. | |
| 6,709,854 B2 | 3/2004 | Donahue, Jr. et al. | |
| 7,339,090 B2 | 3/2008 | Christmann | |
| 7,591,997 B2 * | 9/2009 | Boman | A61K 38/1709 424/184.1 |
| 7,700,308 B2 | 4/2010 | Dale-Crunk et al. | |
| 8,440,207 B2 | 5/2013 | Bermudes | |
| 8,669,085 B2 | 3/2014 | Yang et al. | |
| 8,796,323 B2 | 8/2014 | De Leeuw et al. | |
| 9,125,875 B2 | 9/2015 | Stahle-Backdahl et al. | |
| 9,358,339 B2 | 6/2016 | Greenberg et al. | |
| 2002/0011673 A1 | 1/2002 | Uzoh | |
| 2003/0007726 A1 | 1/2003 | Kosaka et al. | |
| 2004/0005341 A1 | 3/2004 | Horer et al. | |
| 2008/0028034 A1 | 1/2008 | Currid et al. | |
| 2009/0001801 A1 | 1/2009 | Gold et al. | |
| 2009/0156499 A1 | 6/2009 | Wang | |
| 2011/0195133 A1 | 8/2011 | Chen et al. | |
| 2012/0032976 A1 | 2/2012 | Takanori et al. | |

FOREIGN PATENT DOCUMENTS

WO  2005116203 A2  12/2005

OTHER PUBLICATIONS

Nagaoka et al. "Augmentation of the bactericidal activities of human cathelicidin CAP18/LL-37-derived antimicrobial peptides by amino acid substitutions" Inflamm. res. 54 (2005) 66-73 (Year: 2005).*
Held et al. "Kinetic Analysis of β-Galactosidase Activity using the PowerWave™ HT and Gen5™ Data Analysis Software" www.biotek.com, 5 pgs (Year: 2007).*
Zhang et al. "The human cathelicidin LL-37 enhances airway mucus production in chronic obstructive pulmonary disease" Biochemical and Biophysical Research Communications 443 (2014) 103-109 (Year: 2014).*
Nireesha et al. "Lyophilization/Freeze Drying—An Review" IJNTPS vol. 3, num 4, 2013 (Year: 2013).*
Almaaytah, A., Tarazi, S., Abu-Alhaijaa, A., Altall, Y., Alshar'i, N., Bodoor, K., & Al-Balas, Q. (2014). Enhanced antimicrobial activity of Aam AP1-Lysine, a novel synthetic peptide analog derived from the scorpion venom peptide AP1. Pharmaceuticals, 7(5), 502-516. https://doi.org/10.3390/ph7050502.
Choi, O., Lee, Y., Han, I., Kim, H., Goo, E, Kim, J., & Hwang, I. (2013). A simple and sensitive biosensor strain for detecting toxoflavin using β-galactosidase activity. Biosensors and Bioelectronics, 50, 256-261. https://doi.org/10.1016/j.bios.2013.06.058.
Je, J. Y., & Kim, S. K. (2006). Chitosan derivatives killed bacteria by disrupting the outer and inner membrane. Journal of Agricultural and Food Chemistry, 54(18), 6629-6633. https://doi.org/10.1021/jf061310p.

(Continued)

*Primary Examiner* — Thane Underdahl
(74) *Attorney, Agent, or Firm* — Dogwood Patent and Trademark Law; Ashley D. Johnson

(57) ABSTRACT

The presently disclosed subject matter is directed to an assay that detects and quantitatively determines the activity of a lytic peptide that exhibits antimicrobial activity, such as LL-37. Particularly, the assay comprises inducing and/or transfecting bacteria to produce high levels of an enzyme, such as β-galactosidase. The bacteria are then preserved by lyophilization. After a desired amount of time, the bacteria are hydrated with a target sample from a subject suspected of having a specific disease or disorder characterized by an increase in levels of lytic peptide. In the presence of lytic peptide, the enzyme is released from the interior of the bacteria, which can then be detected by alteration of the enzyme substrate. In the absence of lytic peptide, the enzyme remains within the bacteria and no detection of the enzyme occurs.

20 Claims, 9 Drawing Sheets

(56) References Cited

OTHER PUBLICATIONS

M Kahlenberg et al.: Little Peptide, Big Effects: the role of LL-37 in inflammation and Autoimmune Disease, J. Immunol. 2013; 191: 4895-4901).

Dürr, U. H. N., Sudheendra, U. S., & Ramamoorthy, A. (2006). LL-37, the only human member of the cathelicidin family of antimicrobial peptides. Biochimica et Biophysica Acta—Biomembranes. https://doi.org/10.1016/j.bbamem.2006.03.030.

Golec, M. (2007). Cathelicidin LL-37: LPS-neutralizing, pleiotropic peptide. Annals of Agricultural and Environmental Medicine.

Bucki, R., Leszczyńska, K., Namiot, A., & Sokotowski, W. (2010). Cathelicidin LL-37: A multitask antimicrobial peptide. Archivum Immunologiae et Therapiae Experimentalis. https://doi.org/10.1007/s00005-009-0057-2.

Hsieh, I. N., & Hartshorn, K. L. (2016). The role of antimicrobial peptides in influenza virus infection and their potential as antiviral and immunomodulatory therapy. Pharmaceuticals, 9(3). https://doi.org/10.3390/ph9030053.

Fabisiak, A., Murawska, N., & Fichna, J. (2016). LL-37: Cathelicidin-related antimicrobial peptide with pleiotropic activity. Pharmacological Reports, 68(4), 802-808. https://doi.org/10.1016/j.pharep.2016.03.015.

Lee, C. C., Sun, Y., Qian, S., & Huang, H. W. (2011). Transmembrane pores formed by human antimicrobial peptide LL-37. Biophysical Journal. https://doi.org/10.1016/j.bpj.2011.02.018.

Koczulla, R., Von Degenfeld, G., Kupatt, C., Krötz, F., Zahler, S., Gloe, T., . . . Bals, R. (2003). An angiogenic role for the human peptide antibiotic LL-37/hCAP-18. Journal of Clinical Investigation. https://doi.org/10.1172/JCI17545.

Coffelt, S. B., Watson, K., zu Bentrup, K. H., Henkle, S. L., Marini, F. C., Zwezdaryk, K. J., . . . Scandurro, A. B. (2009) The pro-inflammatory peptide LL-37 promotes ovarian tumor progression through recruitment of multipotent mesenchymal stromal cells. Proceedings of the National Academy of Sciences. https://doi.org/10.1073/pnas.0900244106.

Chromek, M., Slamová, Z., Bergman, P., Kovács, L., Podracká, L., Ehrén, I., . . . Brauner, A. (2006). The antimicrobial peptide cathelicidin protects the urinary tract against invasive bacterial infection. Nature Medicine. https://doi.org/10.1038/nm1407.

Bandurska, K., Berdowska, A., Barczyriska-Felusiak, R., & Krupa, P. (2015). Unique features of human cathelicidin LL-37. BioFactors. https://doi.org/10.1002/biof.1225.

Reinholz, M., Ruzicka, T., & Schauber, J. (2012). Cathelicidin LL-37: An antimicrobial peptide with a role in inflammatory skin disease. Annals of Dermatology. https://doi.org/10.5021/ad.2012.24.2.126.

Wu, W. K. K., Wang, G., Coffelt, S. B., Betancourt, A. M., Lee, C. W., Fan, D., . . . Cho, C. H. (2010). Emerging roles of the host defense peptide LL-37 in human cancer and its potential therapeutic applications. International Journal of Cancer. https://doi.org/10.1002/ijc.25489.

Piktel, E., Niemirowicz, K., Wnorowska, U., Wątek, M., Wollny, T., Głuszek, K., . . . Bucki, R. (2016). The Role of Cathelicidin LL-37 in Cancer Development. Archivum Immunologiae et Therapiae Experimentalis. https://doi.org/10.1007/s00005-015-0359-5.

Duplantier, A. J., & van Hoek, M. L. (2013). The human cathelicidin antimicrobial peptide LL-37 as a potential treatment for polymicrobial infected wounds. Frontiers in Immunology. https://doi.org/10.3389/fimmu.2013.00143.

Scott, A., Weldon, S., Buchanan, P. J., Schock, B., Ernst, R. K., McAuley, D. F., . . . Taggart, C. C. (2011). Evaluation of the ability of LL-37 to neutralise LPS in vitro and Ex vivo. PLoS ONE. https://doi.org/10.1371/journal.pone.0026525.

\* cited by examiner

LYTIC PEPTIDE BIOSENSOR AND METHODS OF MAKING AND USING THE SAME

CROSS-REFERENCE TO RELATED APPLICATIONS

This application claims priority to U.S. Provisional Patent Application Ser. No. 62/650,011, filed Mar. 29, 2018, the entire content of which are hereby incorporated by reference.

TECHNICAL FIELD

The presently disclosed subject matter relates to a stable biosensor for the detection and quantitative measurement of the activity of one or more antimicrobial lytic peptides.

BACKGROUND

Antimicrobial peptides (AMPs) are part of the innate immune response found among all classes of life. In humans, AMPs exhibit a broad spectrum of antibiotic activity against gram-positive bacteria, gram-negative bacteria, fungi, certain viruses, and transformed cancerous cells. In humans, the AMP cathelicidin is produced by innate immune cells and epithelial cells and is stored in granules and lamellar bodies. Pro-inflammatory signals produced by innate immune cells responding to the presence of pathogens are received by surface receptors on additional immune and epithelial cells to trigger release of cathelicidin into extracellular fluids. Cathlecidin is then cleaved by proteinase 3 activity from neutrophils and kallikrein in keratinocytes. The N-terminal 37 amino acid peptides that are released then aggregate to form the anti-microbial alpha-helical LL-37 peptide (LL-37).

LL-37 is characterized by the presence of inter-chain disulfide linkages that increase stability and resistance to proteolytic degradation. The LL-37 peptide is positively charged and has been shown to associate with negatively charged phospholipid membranes. Upon interaction with microbial membranes, the alpha-helical shape of LL-37 exposes hydrophobic residues that allow the peptide to penetrate into the lipid layers of membranes. Such penetration results in the formation of trans-membrane pores that lead to bacterial death due to leakage of the bacterial cytoplasmic contents.

In addition to the anti-microbial effect, LL-37 exhibits additional health benefits. For example, the peptide functions to neutralize the endotoxin lipopolysaccharide (LPS) present in gram-negative bacteria, decreases inflammation, and plays an active role in tissue remodeling. Further, LL-37 is angiogenic, thereby inducing neovascularization for accelerated wound healing. The peptide additionally promotes proliferation of epithelial cells lining the respiratory and urogenital tracts, and aids in the repair of damaged airway epithelium by releasing cytokines that attract wound healing macrophages. Due to the ability to neutralize LPS and act as an anti-inflammatory mediator, LL-37 alleviates chronic illnesses such as chronic obstructive pulmonary disease (COPD) and asthma.

Elevated levels of LL-37 are therefore associated with autoimmune diseases, such as psoriasis and systemic lupus erythematosus. Elevated levels of LL-37 are further associated with the hypersensitivity response to allergens and the LPS-containing airborne microparticles observed in asthma. Therefore, overexpression of the peptide is believed to be linked to such inflammatory diseases. Toll-like receptor (TLR) signaling is required for the development of autoimmunity, and thus a decrease in TLR signaling (especially by binding of LPS and blocking of TLR4 receptor complex formation by LL-37) exerts an anti-inflammatory effect through dendritic cells and macrophages. Lytic peptides also exert activity toward enveloped viruses, such as influenza. Research has further shown that LL-37 has a function in the progression of cancers. LL-37 therefore plays an important role as an antimicrobial peptide and anti-inflammatory agent in autoimmune and hypersensitivity diseases.

It would therefore be beneficial to provide a method of detecting and/or quantifying one or more lytic peptides, such as LL-37 or a peptide with a similar membrane lytic mechanism of action.

SUMMARY

In some embodiments, the presently disclosed subject matter is directed to an in vitro method for detecting the presence of membrane lytic peptide in a sample. The method comprises inducing bacterial cells to express an enzyme by incubating in induction media. The method further includes lyophilizing the bacterial cells. The method comprises contacting the lyophilized bacterial cells with the sample, wherein the sample comprises an amount of the membrane lytic peptide and a substrate that produces a color change in the presence of the enzyme. The method further includes incubating the bacterial cells with the sample for a desired amount of time. The method comprises detecting the presence of the membrane lytic peptide in the sample by colorimetric analysis.

In some embodiments, the membrane lytic peptide is an antimicrobial peptide. The term "antimicrobial peptide" refers to a peptide that exhibits inhibitory activity. Thus, the antimicrobial peptide can include any peptide having antibacterial, anti-fungal, anti-parasitic, anti-viral, bactericidal, algicidal, amebicide, microbicidal, bactericidal, fungicidal, parasiticidal.

In some embodiments, the membrane lytic peptide is human or synthetic LL-37. The term "of human origin" refers to any natural form of the peptide (found in humans or obtained after culturing human cells. The term "of synthetic origin" refers to a material that has not be produced or synthesized by a living organism directly.

In some embodiments, the enzyme is β-galactosidase and the substrate is 5-bromo-4-chloro-3-indolyl-β-d-galactopyranoside.

In some embodiments, the color change comprises a blue color in the presence of the enzyme.

In some embodiments, the lyophilization comprises reducing the temperature of the bacterial cells in incubation media to the triple point.

In some embodiments, the incubating is for 1 hour or less.

In some embodiments, the presently disclosed subject matter is directed to a biosensor comprising bacterial cells induced to express an enzyme, an inducing agent to induce expression of the enzyme, one or more lytic agents, and culture media. The term "biosensor" refers to a system or device that allows for detection of a target (e.g., a membrane lytic peptide), wherein the biosensor combines a biological component (e.g., bacterial cells induced to express an enzyme) and a physiochemical detector (e.g., x-gal) that interacts with the enzyme to produce a detectable change (e.g., a color change) upon contact.

In some embodiments, the presently disclosed subject matter is directed to a kit comprising bacterial cells induced to express an enzyme, an inducing agent to induce expression of the enzyme, one or more lytic agents, and culture media. In some embodiments, the kit further comprises a detection agent (e.g., X-gal) that interacts with the enzyme to produce a detectable change (e.g., a color change) upon contact.

In some embodiments, the enzyme is β-galactosidase.

In some embodiments, the inducing agent is isopropyl β-D-1-thiogalactopyranoside (IPTG).

In some embodiments, the one or more lytic agents are selected from human LL-37, synthetic LL-37, or combinations thereof.

In some embodiments, the presently disclosed subject matter is directed to a method of detecting a chronic condition or disorder in a subject, wherein the chronic condition or disorder is characterized by the presence of an antimicrobial membrane lytic peptide. Particularly, the method comprises inducing bacterial cells to express an enzyme. The method includes lyophilizing the bacterial cells. The method comprises obtaining a sample from the subject, wherein the sample is selected from blood, saliva, urine, or combinations thereof. The method comprises contacting the lyophilized bacterial cells with the sample, wherein the sample comprises an amount of the antimicrobial membrane lytic peptide. The method comprises contacting the lyophilized bacterial cells with a substrate that produces a color change in the presence of the enzyme. The method comprises incubating the bacterial cells for a desired amount of time. The method comprises detecting the chronic condition or disorder in the subject by colorimetric analysis of the color change in the sample.

In some embodiments, the antimicrobial membrane lytic peptide is human or synthetic LL-37.

In some embodiments, the enzyme is β-galactosidase and the substrate is 5-bromo-4-chloro-3-indolyl-β-d-galactopyranoside.

In some embodiments, the color change comprises a blue color in the presence of the enzyme, indicative of the presence of the chronic condition or disorder in the sample.

In some embodiments, the chronic condition or disorder is selected from one or more of chronic obstructive pulmonary disease (COPD), asthma, psoriasis, systemic lupus erythematosus, and cancer progression.

In some embodiments, the lyophilization comprises reducing the temperature of the bacterial cells in incubation media to the triple point.

In some embodiments, the incubating is for 1 hour or less. In some embodiments, the presently disclosed subject matter is directed to a standardized method of measuring the activity of a membrane lytic peptide toward membranes of bacteria and other organisms with an enclosing membrane. The disclosed method utilizes an enzyme present within a bacterial or microbial culture, such that release of the enzyme indicates activity of the lytic agent. For example, the method includes co-culturing β-galactosidase-induced bacteria with a lytic peptide or agent, incubating, and adding a colorimetric substrate (e.g., X-gal) that binds to the enzyme present in the supernatant due to membrane lysis.

In some embodiments, the presently disclosed subject matter is directed to a method of observing the ability of a bacterial culture to produce a metabolic enzyme that is induced and released upon lysis of the cell membrane by a lytic agent, in the presence of a peptide. As demonstrated by the culturing of LAcZ+E. coli in IPTG and glucose deprived media, IPTG is a molecular mimic of allolactose. IPTG binds to the lac repressor and releases the tetrameric repressor from the lac operator in an allosteric manner, thereby allowing the transcription of genes in the lac operon, such as the gene coding for beta-galactosidase. Unlike allolactose, the sulfur atom creates a chemical bond that is non-hydrolyzable by the cell, preventing the cell from metabolizing or degrading the inducer. A lytic agent is used to permeate the membrane thereby causing B-galactosidase to leak out of the cell into the supernatant; where a colorimetric substrate X-gal binds to the enzyme and produces a blue color.

In some embodiments, the presently disclosed subject matter is directed to a method of lyophilizing (e.g., freeze-drying) a standardized bacterial culture under vacuum for use in an enzyme release assay that detects the presence of an anti-microbial lytic peptide. As demonstrated by the lyophilization of enzyme-carrying bacterial cells (that are later hydrated when ready to use), a lytic agent can be used to permeate the membrane causing the enzyme to move into the supernatant and react with the colorimetric substance X-gal.

In some embodiments, the presently disclosed subject matter is directed to a method for the detection and assay of the release of an enzyme, indicator protein, and/or fluorogenic substance following contact with a membrane lytic agent.

In some embodiments, the presently disclosed subject matter is directed to a method for detection and activity measurement of a lytic peptide or lytic agent that plays a role in human diseases and/or disorders.

In some embodiments, the presently disclosed subject matter is directed to a method of detecting and measuring the presence and/or concentration of a lytic peptide to detect a corresponding infection by a foreign organism that induces lytic peptides during the infection.

In some embodiments, the presently disclosed subject matter is directed to a method of detecting the presence and quantity of a lytic peptide that is produced within or released by immune or epithelial cells.

In some embodiments, the presently disclosed subject matter is directed to a method of determining the level of a peptide that can neutralize the effects of inflammatory substances, such as endotoxin or lipopolysaccharide from bacteria and other microbes.

In some embodiments, the presently disclosed subject matter is directed to a method that comprises the use of an enzyme substrate that interacts with the release of an enzyme or fluorogenic substance from microbial cells induced or transfected with the enzyme or a fluorogenic substance.

In some embodiments, the presently disclosed subject matter is directed to a method for the detection and measurement of a lytic substance or peptide that plays a role in the progression of cancer.

BRIEF DESCRIPTION OF THE DRAWINGS

The previous summary and the following detailed descriptions are to be read in view of the drawings, which illustrate some (but not all) embodiments of the presently disclosed subject matter.

DETAILED DESCRIPTION

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "an assay" can include a plurality of such assays, and so forth.

Unless otherwise indicated, all numbers expressing quantities, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed system and methods.

The presently disclosed subject matter is directed to a system and method of detecting and quantitatively determining the activity of a lytic peptide that exhibits antimicrobial activity, such as (but not limited to) LL-37. The phrase "antimicrobial activity" refers to the property or capability of a material to inactivate microorganisms (e.g., bacteria, fungi, archaea, protozoans, and/or mycoplasma).

As set forth above, LL-37 plays an important role as an antimicrobial peptide and anti-inflammatory agent in autoimmune and hypersensitivity diseases. See, for example, U.S. Pat. No. 9,125,875, the entire content of which is incorporated by reference herein.

Figure 1:
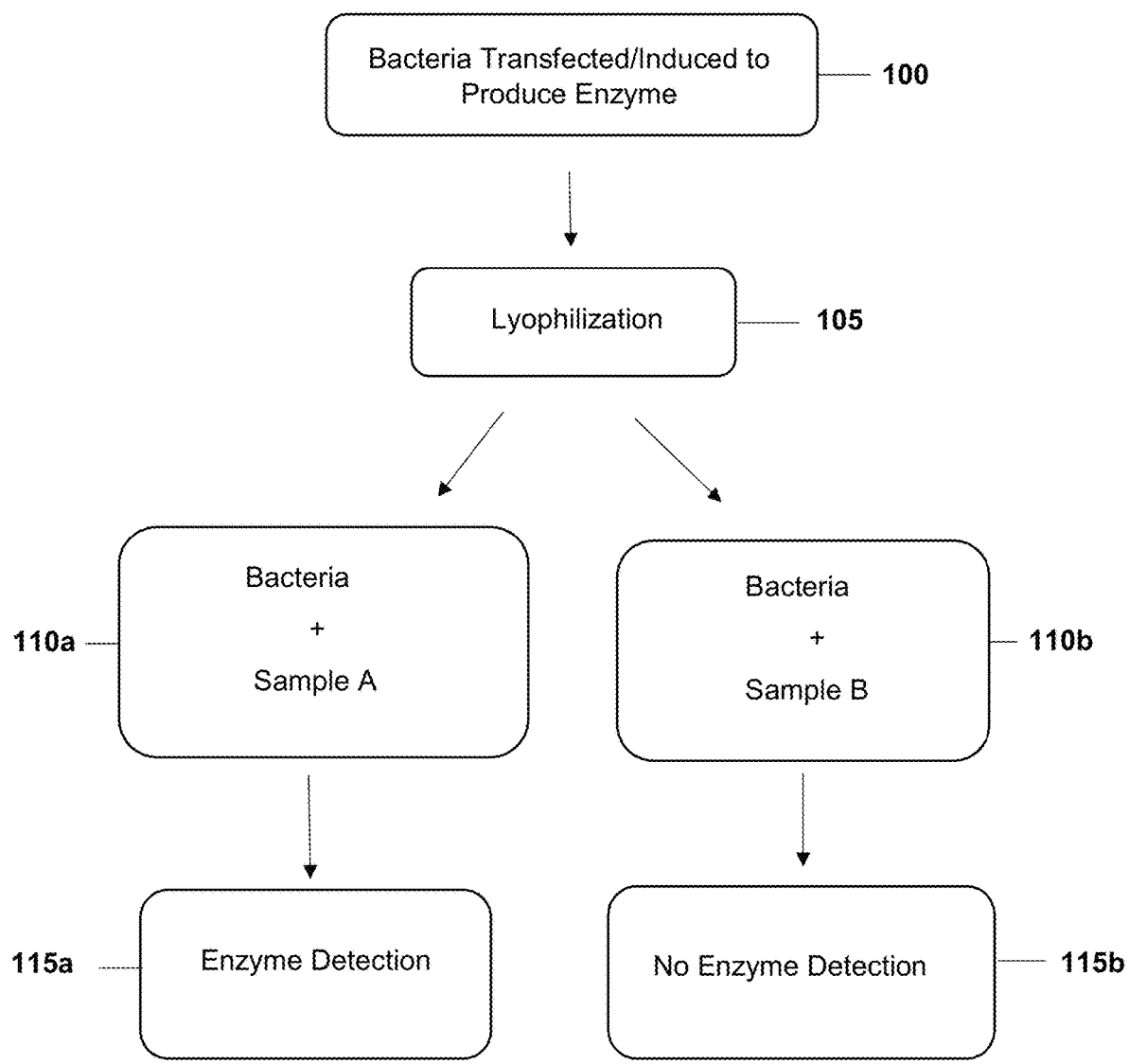
FIG. 1 is a schematic illustrating an assay that can be used to detect the presence or absence of a lytic peptide in accordance with some embodiments of the presently disclosed subject matter.

FIG. 1 illustrates a schematic of one method of using the disclosed assay. Particularly, at step 100 bacteria is induced and/or transfected to produce high levels of a detection enzyme. The bacteria are then preserved by lyophilization at step 105. As shown in step 110a, the bacteria can be hydrated with Sample A that comprises an amount of a membrane lytic peptide and an enzyme substrate. By interacting with the cell membranes of the bacteria, the lytic peptide causes the release of the enzyme present within the bacteria. The enzyme is then detected by alteration of the enzyme substrate, as illustrated in step 115a. As shown in steps 110b and 115b, when the sample lacks an amount of lytic peptide (Sample B), the enzyme remains within the bacteria and no detection of the enzyme occurs.

As described, the disclosed assay comprises a first step of inducing and/or transfecting bacteria to produce high levels of a desired enzyme. As used herein, the term "inducing" or "induction" refers to the introduction of a signal that results in a change in the morphology and/or physiology of a cell (e.g., the transcription of a specific gene or the production of a protein after exposure to a specific stimulus). In some embodiments, the induction can be accomplished through the use of isopropyl β-D-1-thiogalactopyranoside (IPTG). Particularly, IPTG is an inducer of β-galactosidase activity in bacteria. See, for example, U.S. Pat. Nos. 4,070,247 and 6,284,484, the entire contents of which are incorporated by reference herein. The inducer can be present at a concentration of about 0.1-1 mmol/L. Bacteria can be induced in any suitable cell culture media (e.g., RPMI 1640, available from ThermoFisher Scientific, Waltham, Mass.), such as in a tube and later transferred to a plate (e.g., a 96 well plate) following incubation. The incubation period can be about 1 hour, such (but not limited to) about 30 minutes to about 4 hours (e.g., about 0.5, 1, 1.5, 2, 2.5, 3, 3.5, or 4). However, it should be appreciated that the incubation time can be greater or less than the range given herein.

As would be appreciated by those of ordinary skill in the art, the term "transfection" refers to the introduction of foreign DNA into cells (e.g., a bacterial cell). Transfection can be accomplished using any method known or used in the art, including (but not limited to) calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment), and the like. See, for example, U.S. Pat. Nos. 5,593,875; 7,339,090; 6,171,862; 8,669,085; 6,637,720; 6,709,854; 4,608,339; 8,440,207; 9,358,339; 2004/0053410; 2008/0280340; 2002/0116732; 2003/0077268; 2009/0018016; and PCT Publication Nos. WO2005116203 and WO2016200064, the entire contents of which are incorporated by reference herein.

In some embodiments, bacterial cells can be transfected with competent cells. For example, the E. coli strain J107Δ (Lac Z)M15 can be used because it lacks kanamycin resistance gene and cannot make β-galactosidase until the α peptide is supplied by an intact pK19 plasmid. The competent cells can be spun down. 1 μL of plasmid DNA can be added to the competent cells. The mixture can then be spun down again and placed in the chamber of an electroporator. In some embodiments, the electroporator can be charged to about 405-408 volts (e.g., a current of 2.25-2.5 can be used).

The cells can then be rinsed in LB broth and incubated at 37° C. for 1 hour. The cells can then be spread on a plate that includes kanamycin, IPTG and X-gal. Only cells containing plasmids with the kanamycin resistance gene will grow on these plates. Cells with β-galactosidase activity will be blue and all others will be white.

Alternatively, transfected bacterial cells can be purchased through well known vendors, such as U.S. Biological, Sigma Aldrich, Carolina Biological Supply Company, Thermo Fisher Scientific, and the like.

Any desired bacterial strain can be used for the transfection and/or induction. For example, suitable bacteria can be selected from one or more of *Streptococcus* (e.g., *S. pyrogenes, S. pneumoniae*), *Enterococcus, Staphlyococcus* (e.g., *S. aureus*), *Escherichia* (e.g., *E. coli*), *Salmonella* (e.g., *S. enterica, S. bongori*), *Yersinia* (e.g., *Y. enterocolitica*), *Vibrio* (e.g., *V. parahaemolyticus*), *Pseudomonas* (e.g., *P. aeruginosa*), and *Bacillus* (e.g., *B. subtilis, B. cereus*). It should be appreciated that the above list is not exhaustive, and any desired bacterial strain can be used. In some embodiments, the *E. coli* strain K12 can be used. See, for example, *The Complete Genome Sequence of Escherichia coli* K-12, Blattner et al., Science, 277:1453-1462 (1997), incorporated herein by reference.

Further, any sac enclosed with a membrane can be used to transfect the enzyme, such as (but not limited to) liposomes. The term "liposome" refers to refers to phospholipid vesicles comprising one or more (e.g., 1-3) phospholipid bilayer membranes. Representative liposomes include (but are not limited to) 1,2-dimyristol-sn-glycero-3-phosphocholine (DM PC), 1-palm itoyl-2-oleoyl-sn-glycero-3-phosphocholine (POPC), Hydrogenated soybean phosphatidylcholine (HSPC), (DOPC), 1,2-Distearoyl-sn-glycero-3-phosphocholine (DSPC), 1,2-Dipalmitoyl-sn-glycero-3-phosphocholine (DPPC), and/or 1-Stearoyl-2-oleoyl-sn-glycero-3-phosphocholine (SOPC), optionally coated with polyethylene glycol (PEG) to reduce non-specific binding of serum proteins and to prolong circulation time. Temperature-sensitive liposomes can also be used, as disclosed in U.S. Pat. No. 6,200,598, incorporated by reference herein. In some embodiments, the liposomes can include radiotracers, contrast agents, chromophores, dyes, enzyme substrates, therapeutic agents, chemotherapeutic agents and/or DMA segments.

The bacteria can be transfected/induced to produce one or more suitable enzymes. The term "enzyme" refers to any protein that catalyzes a chemical reaction. For example, in some embodiments, the bacteria can be transfected with the gene that expresses the enzyme β-galactosidase. β-galactosidase is a glycoside hydrolase enzyme that catalyzes the hydrolysis of β-galactosides into monosaccharides through the rupture of a glycosidic bond. β-galactosidase can be detected using the chromogenic substrate 5-bromo-4-chloro-3-indolyl-β-d-galactopyranoside (X-gal). Specifically, β-galactosidase cleaves the glycosidic bond in X-gal and forms galactose and 5-bromo-4-chloro-3-hydroxyindole which dimerizes and oxidizes to 5,5'-dibromo-4,4'-dichloro-indigo, an intense blue product that is easy to identify and quantify.

Thus, in some embodiments, the β-galactosidase enzyme is produced by the transfected bacterial cell and remains within the cell until released, such as through the action of a lytic membrane protein as described in detail below.

The disclosed method further comprises a lyophilization step. The term "lyophilization" refers to a drying process that includes freezing a material dissolved in lyophilization fluid below 0° C. and then reducing the surrounding pressure using a vacuum pump to allow the frozen water in the solution to sublimate and/or evaporate. In some embodiments, lyophilization can be referred to as "freeze drying." Advantageously, the lyophilization process allows recovery of the desired activity (i.e., enzyme activity) after the freezing process. Any known lyophilization method can be used. For example, bacteria can be induced, as described herein below. After a period of incubation (e.g., 1 hour), the cells can be resuspended and a portion (e.g., 1 mL) of the culture aliquoted into a series of Eppendorf tubes. The tubes can be placed in a SpeedVac (lypholizer), the centrifuge turned on, vacuum applied, and the cells lyophilized for a predetermined time/temperature (e.g., 12 hours at −40° C.).

Importantly, the lyophilization step preserves the bacteria to be rehydrated and reused at a later time without compromising the bacterial membrane integrity, which has proven to be especially beneficial when provided in a kit or assay. Leaving the bacteria suspended in medium in a plate with relatively low volume quickly invokes membrane deterioration and therefore compromises the assay, as the enzyme merely leaks out without any response to a lytic agent. Therefore, lyophilization aids in preservation and maintaining membrane integrity for long periods of time (two weeks or longer has been confirmed). In contrast, leaving the cells suspended in media in the absence of any lytic agent will cause membrane deterioration in about 3 hours.

Thus, the transfected/induced bacteria are added to a vessel for lyophilization. In some embodiments, the lyophilization fluid is selected from one or more of water, buffer (e.g., phosphate buffered saline), or combinations thereof. In some embodiments, the cells can be lyophilized directly in an induction media, such as cell culture medium that includes an induction agent (e.g., RPMI 1640 medium (−) glucose and IPTG). The term "induction media" refers to medium suitable for inducing cells (e.g., media comprising IPTG). The lyophilization fluid provides a stabilizing environment for the bacteria for a finite time before lyophilization. The fluid further provides favorable thermal and freezing properties during lyophilization and cryoprotects the desired activity of the enzyme. In some embodiments, the pH of the solution is between about 6.8 and 8.2.

Figure 2:
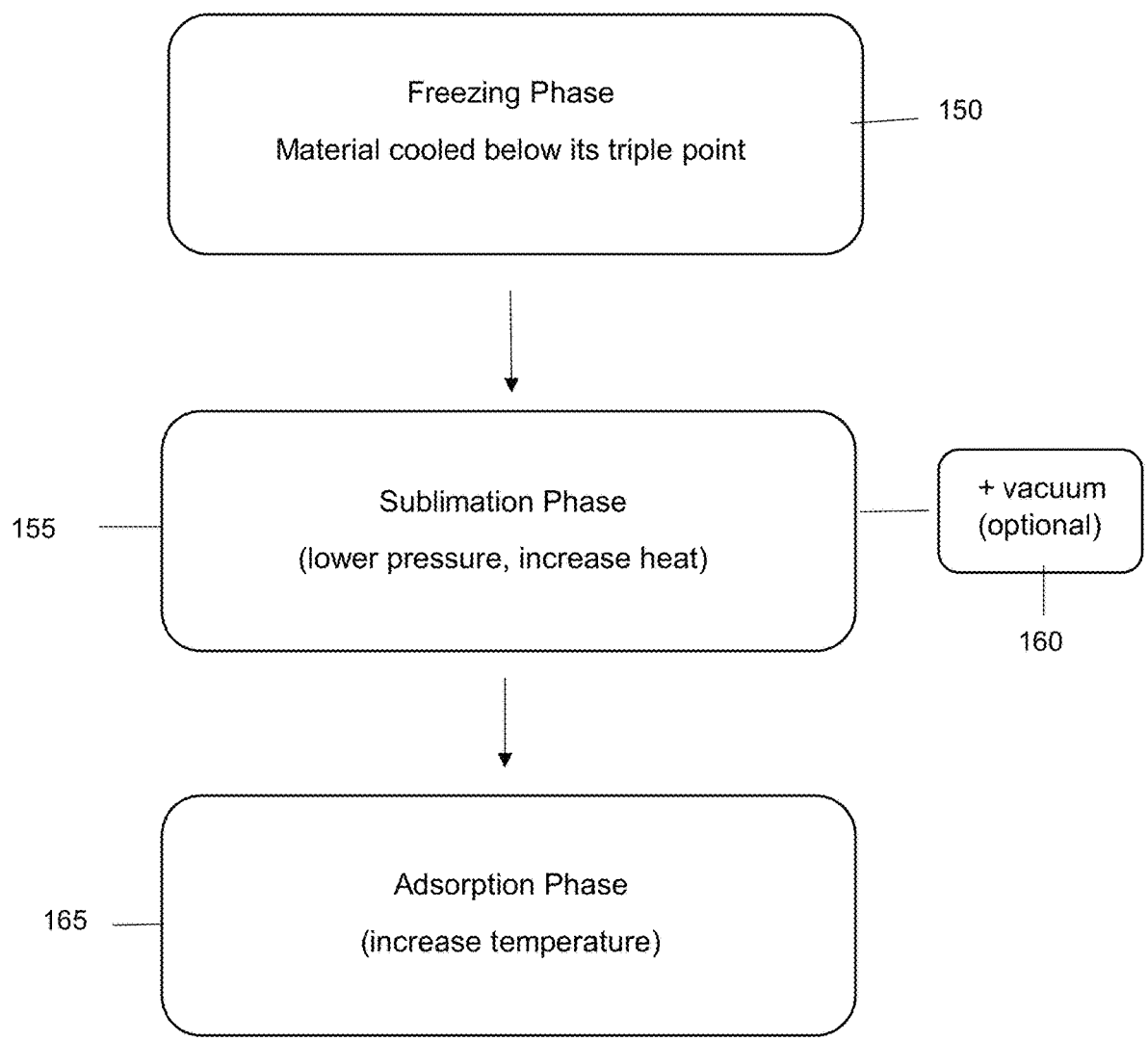
FIG. 2 is a schematic illustrating one method of lyophilization of cells (e.g., bacterial cells) in accordance with some embodiments of the presently disclosed subject matter.

One method of lyophilization that can be used is illustrated in FIG. 2. Particularly, the first phase is freezing phase 150, where the product is frozen. Any suitable method can be used to freeze the bacterial cells, including use of a freezer, chilled bath (shell freezer), or on a shelf in a freeze-dryer. Cooling the material below its triple point ensures that sublimation (rather than melting) will occur to preserve the physical form of the material. The triple point of a material is temperature and pressure at which the three phases (gas, liquid, and solid) of a substance coexist in thermodynamic equilibrium. Further, the triple point is the temperature and pressure at which the sublimation curve, fusion curve, and the vaporization curve meet.

As shown in FIG. 2, after the freezing phase, the product enters a primary drying (sublimation) phase 155. In this phase, the pressure is reduced and heat is added to allow the water to sublimate. In some embodiments, vacuum 160 can be used to speed sublimation. A cold condenser can be used to provide a surface for the water vapor to adhere and solidify. The condenser also protects the vacuum pump from the water vapor. In some embodiments, about 95% of the water in the material is removed.

In some embodiments, the third phase of lyophilization is secondary drying (adsorption) phase 165, as shown in FIG. 2. In this phase, the ionically-bound water molecules are removed. By raising the temperature higher than the primary drying phase, the bonds between the material and the water molecules are broken. Freeze dried materials retain a porous structure. After the lyophilization process is complete, the vacuum can be broken (e.g., with an inert gas) before the material is sealed. Most materials can be dried to 1-5% residual moisture.

After the lyophilization step, the disclosed method comprises hydrating the bacteria with a target solution that includes an amount of lytic peptide. The term "lytic peptide" or "membrane lytic peptide" refers to any protein in whole or part that is capable of permeabilizing or disrupting a bacterial cell membrane. In some embodiments, the lytic peptide is human in origin. However, the presently disclosed subject matter also includes embodiments wherein the lytic peptide is synthetic in origin.

Figure 3A:
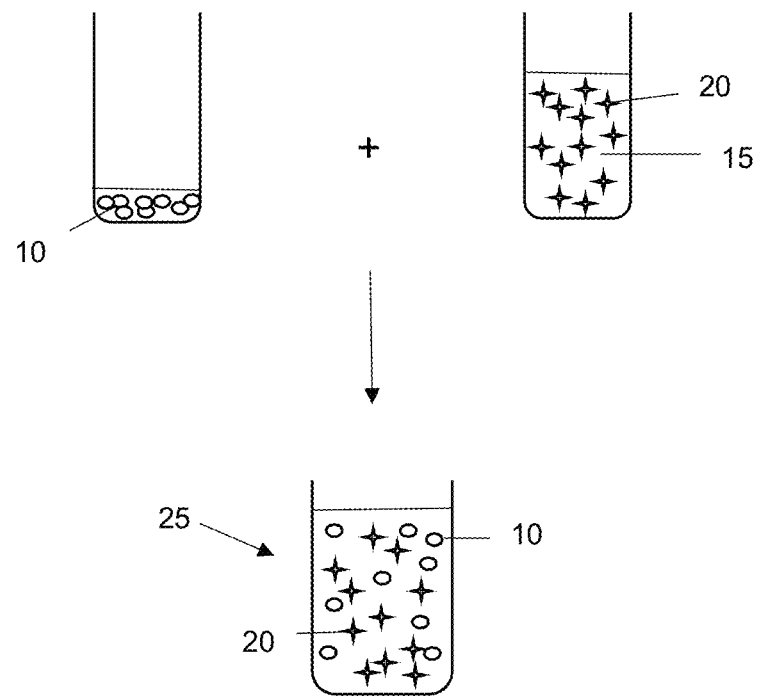
FIG. 3a-3c are schematics illustrating one embodiment of the disclosed system and method.
Figure 3B:
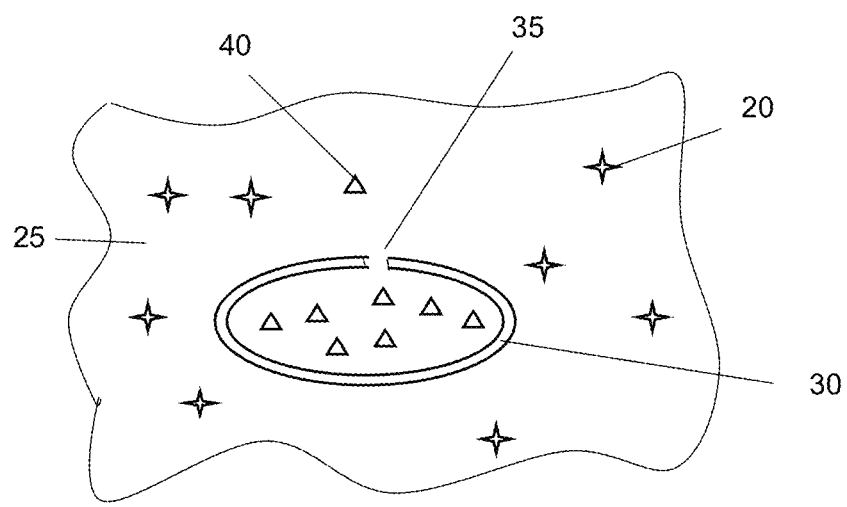

The term "target solution" refers to a sample solution from a subject suspected of having elevated levels of a lytic peptide, which can be indicative of a disease or disorder. For example, the target solution can comprise a blood, urine, and/or saliva sample. In some embodiments, the sample solution can be a lytic agent solution in PBS (e.g., about 1000 μL of a 200 μM lytic agent solution). By interacting with the cell membranes of the bacteria, the lytic peptide in the target solution causes the release of the enzyme present within the target bacterium. Specifically, in the presence of target solution that comprises a threshold amount of lytic peptide, the peptide disrupts the bacterial cell membrane, forming a pore. As a result, enzyme produced by the bacteria (e.g., β-galactosidase) is released from the bacterial cell. For example, as shown in FIG. 3a, lyophilized bacteria 10 is contacted with sample 15 comprising a threshold amount of lytic peptide 20 to produce solution 25. As shown in FIG. 3b, when solution 25 comprises a threshold amount of lytic peptide 20, the lytic peptide ruptures bacterial cell membrane 30 to form pore 35, such that enzyme 40 is released into the solution.

Figure 3C:
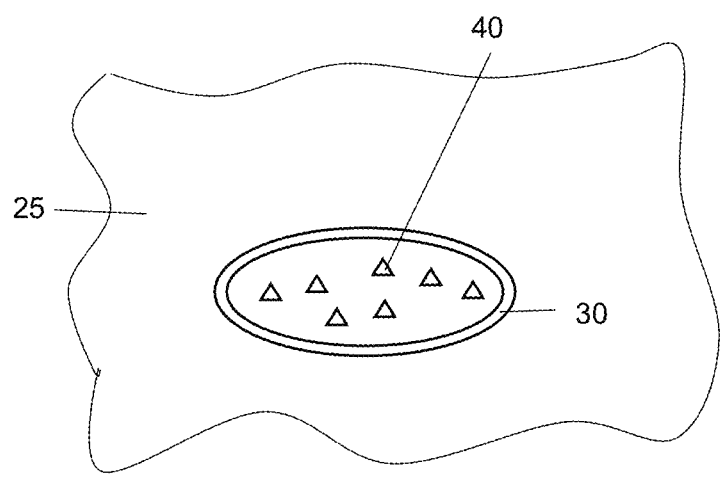

Conversely, in the absence of a threshold level of lytic peptide (e.g., LL-37), the bacterial cell membrane remains intact and the enzyme remains housed within the interior of the bacterial cell, as illustrated in FIG. 3c.

Any suitable lytic peptide can be used in the disclosed assay, such as (but not limited to) LL-37, α-Defensin HNP-1, α-Defensin HNP-2, α-Defensin, HNP-3 Histatin 1, Histatin 3, α-Defensin HNP-4, RNase 2, RNase 3 (Eosinophil cationic protein, ECP), α-Defensin HD-5, α-Defensin HD-6, β-Defensin hBD-1, Cathelicidin LL-37, β-Defensin hBD-2, Granulysin, Ubiquicidin, Thrombocidin-1 (TC-1), Hepcidin 25 (LEAP-1), β-Defensin hBD-3, β-Defensin hBD-4, Dermcidin, RNase 7, RNase 5 (angiogenin), Chemokine CCL20, Chemokine CXCL9, RegIIIa, Drosomycin-like defensin (DLD), Elafin, β-amyloid peptide 1-42, Chemerin, Amylin, KDAMP, and DEFB114. See, for example, U.S. Pat. Nos. 7,700,308; 8,796,323; 5,734,014; 2011/0195133; 2012/0329760, the entire contents of which are incorporated by reference herein.

In some embodiments, the target solution comprising an amount of lytic peptide can be incubated with the lyophilized bacteria for a period of about 1-60 minutes, such as about 5-45, 10-30, or about 15 minutes. Thus, the target solution can be incubated with the bacteria for at least about (or no more than about) 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 minutes. It should be appreciated that the disclosed range is not limiting, and the incubation step can occur for periods of time longer (e.g., 1, 1.5, 2, 2.5, 3, 3.5, 4 or more hours) or shorter than the range set forth above.

In some embodiments, the incubation step can occur at room temperature, such as about 15-25° C. However, the incubation can occur at temperatures greater or less than room temperature (1-14° C. or 26-90° C.). Therefore, the incubation can occur at a temperature of at least about (or no more than about) 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, or 90° C. The disclosed range is not limiting, and the incubation step can occur at temperatures above or below the ranges set forth above.

The method comprises detecting the presence or absence of the enzyme produced by the bacteria. Particularly, in the presence of lytic peptide, the enzyme produced by the bacterial cells is released into solution, allowing detection. For example, β-galactosidase can be detected by interaction with X-gal, producing a blue color. As shown below in Formula (I), X-gal is hydrolyzed by the β-galactosidase enzyme, which cleaves the β-glycosidic bond in D-lactose.

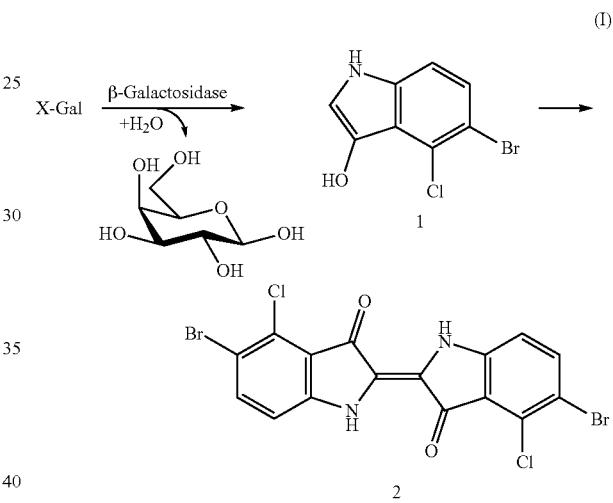

(I)

X-gal, when cleaved by β-galactosidase, yields galactose and 5-bromo-4-chloro-3-hydroxyindole (identified as 1 in Formula I), that spontaneously dimerizes and is oxidized to 5,5'-dibromo-4,4'-dichloro-indigo (identified as 2 in Formula I), which produces an intensely blue color that is insoluble. X-gal itself is colorless, so the presence of a blue-colored product is indicative of the presence of active β-galactosidase. Thus, the detection of the enzyme (e.g., blue color) indicates the presence of an amount of lytic peptide.

Conversely, in the absence of lytic peptide, the enzyme produced by the bacteria remains within the bacterial cell and no detection occurs. That is, the β-galactosidase remains within the bacterial cell and does not react with X-gal to produce a blue color.

In some embodiments, the detection can comprise colorimetric analysis of the reaction (e.g., quantification of a color change from pink to blue). For example, the presence of a blue color is considered a positive indicator for the presence of lytic peptide. Similarly, remaining pink in color is considered a negative for the presence of lytic peptide. Color can be quantified and absorbance measured in a spectrometer at about 570 nm (e.g., about 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, or 700 nm), and results can be determined relative to control (e.g., untreated) absorbance values (e.g., control can have A570 of about 0.008). In some embodiments, an A570 of about 0.15-0.8 can be indicative of a positive result. Thus, an absorbance at 570 nm can be considered a positive indicator of the presence of lytic peptide at values of at least about (or no more than about) 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.3, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, or 0.8.

It should be appreciated that the disclosed system and method is not limited to detection methods that employ a β-galactosidase and X-gal color reaction. Rather, any assay that can detect the presence of β-galactosidase and produce a color change can be used.

Importantly, detection of the presence of lytic peptide in a sample solution can be indicative of one or more chronic conditions or disorders in a subject (e.g., human). For example, elevated levels of the lytic peptide LL-37 has been associated with the presence of autoimmune diseases (such as psoriasis and systemic lupus erythematosus), asthma, viral infection (such as influenza), cancer progression, and the like. For example, compared with the control group, an elevated level of lytic peptide (e.g., LL-37) in human plasma can be at least about 2.0 ng/mL compared to about 1.8 ng/mL control (e.g., at least about 2.0, 2.1, 2.2, 2.3, 2.4, 2.5, 2.6, 2.7, 2.8, 2.9, or 3 ng/mL). Further, elevated levels of lytic peptide (e.g., LL-37) in urine can be at least about 0.3 ng/mg (e.g., at least about 0.3, 0.4, 0.5, 0.6, 0.7, 0.8, 0.9, 1, 1.1, 1.2, 1.3, 1.4, 1.5, 1.6 ng/mg) compared to about 0.0 ng/mg in control urine. See, for example, Babikir, Ibrahim H et al. "The impact of cathelicidin, the human antimicrobial peptide LL-37 in urinary tract infections" *BMC infectious diseases* vol. 18, 1 17. 8 Jan. 2018, doi:10.1186/s12879-017-2901-z, the entire content of which is hereby incorporated by reference herein. The disclosed assay can therefore be used as an assay to detect the presence of one or more diseases or disorders. Positive detection of the lytic peptide is indicative of presence of the condition or disease, and the absence of elevated levels of the lytic protein is indicative of absence of the condition or disorder.

In some embodiments, the disclosed assay can be formulated as a kit for monitoring and/or detecting elevated levels of a lytic peptide in a subject. The kit comprises bacteria transfected with LacZ (e.g., LacZ+*E. coli* cells), an inducing agent to induce expression of the LacZ (e.g., IPTG), culture media, a β-galactosidase colorimetric detection agent (such as X-gal), and synthetic lytic agent (such as LL-37).

The kit can be used in a variety of ways. For example, in some embodiments, liquid bacterial culture (e.g., *E. coli* cells transfected to express the LacZ gene) can be removed from incubation and centrifuged (e.g., about 1200 RPM for about 7 minutes). In some embodiments, the cells can be freeze dried prior to use. The supernatant can then be removed, and the bacterial pellet resuspended liquid tissue culture medium (e.g., in 1 mL of RPMI-1640 without glucose). A centrifuge tube can be prepared with induction media, including liquid culture medium (e.g., about 8.9 mL of RPMI-1640 without glucose) and inducer (such as 100 uL of IPTG). The resuspended bacterial culture can then be added to the new tube. The bacterial culture in the induction media can then be incubated for a desired amount of time at a desired temperature (e.g., about 37° C. for about 0.5, 1, 1.5, 2, 2.5, 3, 3.5, or 4 hours). After incubation, the bacterial culture in induction media can be vortexed and re-suspended. A desired amount (e.g., about 100 μL) can be transferred to one or more wells of an assay plate (e.g., a flat bottomed 96-well plate). In some embodiments, an untreated, negative control can also be added to the plate (e.g., induced bacteria culture). In some embodiments, a negative control can be included (e.g., a 20% stock SDS solution). The plate can then be incubated for a desired time at a desired temperature (e.g., at least about/no more than about 5, 10, 15, 20, 25, 30, 35, 40, 45, 50, 55, or 60 minutes at about 37° C.). After incubation, an aliquot (e.g., about 20 uL) of X-gal substrate is added to each well. Then plate is again incubated (e.g., at least about/no more than about 5, 10, 15, 20, 25, 30, 35, 40, 45, 50, 55, or 60 minutes at about 37° C.). After incubation, the plate can be analyzed for colorimetric results using a qualitative scale, or absorbance to be measured with a spectrophotometer (e.g., at 570 nm) to quantify the color change intensity.

The term "subject" as used herein refers to a biological organism from which a sample can be obtained. For example, in some embodiments, the subject can be a human. However, it should be appreciated that the subject can include any mammal, such as a pig, horse, dog, cat, etc. The subject can further include non-mammals, such as birds, reptiles, and fish.

As set forth above, the disclosed assay is an improved assay for detecting the presence or absence of a lytic peptide (e.g., an antimicrobial lytic peptide) as a marker for a condition or disease. Advantageously, the assay is quick and easy to perform compared to prior art assays. Particularly, prior art assays require the conduction of lengthy ELISA procedures and the growth of bacterial cultures. The disclosed assay does not require bacterial growth or its inhibition, which is time-consuming and requires highly skilled users.

The disclosed assay is also stable and portable, allowing users the convenience and ease of transporting the assay as needed. The assay can therefore be used in a variety of locations, including on-the-spot testing.

Further, the disclosed assay is enzyme-based and sensitive, allowing for reliable results and fewer false positives.

EXAMPLES

The following Examples provide illustrative embodiments. In light of the present disclosure and the general level of skill in the art, those of ordinary skill in the art will appreciate that the following Examples are intended to be exemplary only and that numerous changes, modifications, and alterations can be employed without departing from the scope of the presently disclosed subject matter.

Example 1

Design Feasibility Study

Figure 4A:
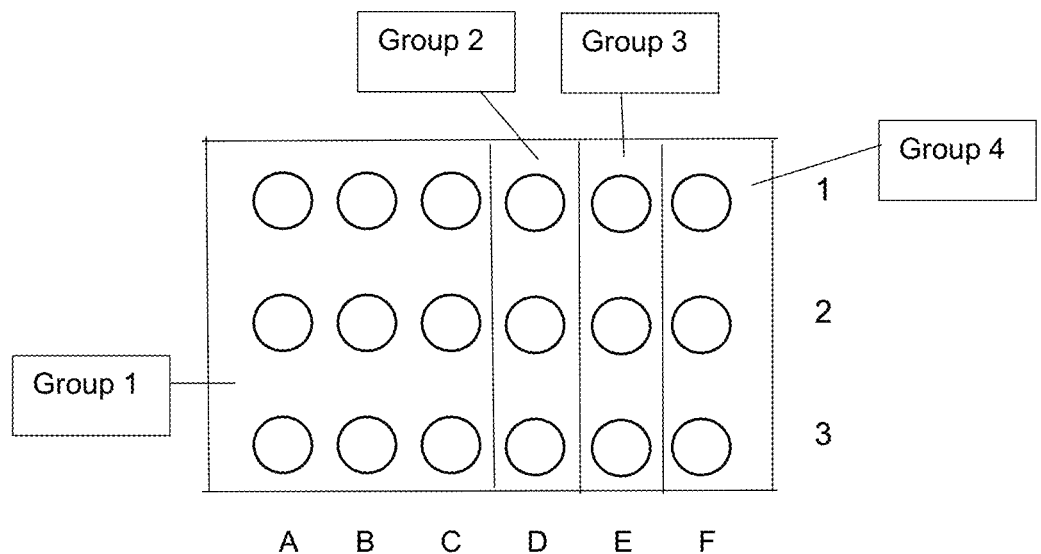
FIG. 4a is a top plan view of a welled plate.
Figure 4B:
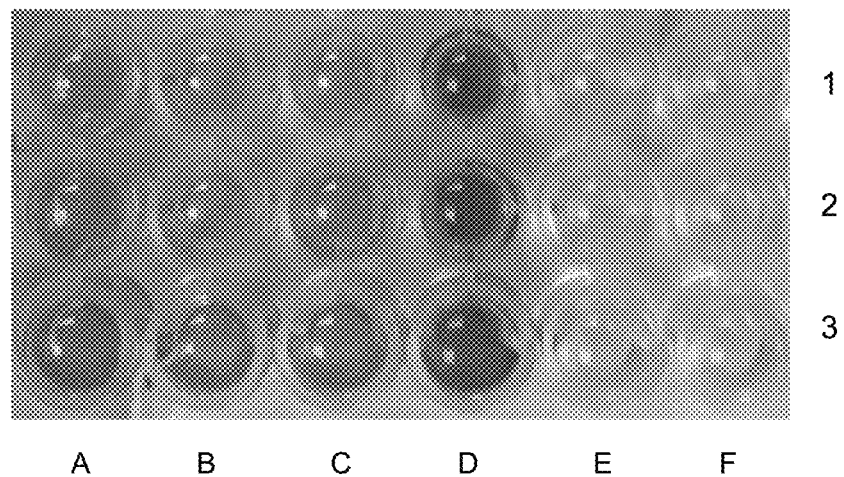
FIG. 4b is a photograph illustrating the plate of FIG. 4a during use.

As shown in FIG. 4*a*, a plate was designed as follows: *E. coli* bacterial cells induced to produce β-galactosidase were deposited in wells A1-A3, B1-B3, C1-C3, D1-D3, and E1-E3. Non-induced *E. coli* cells were deposited in wells F1-F3 (control). The cells were treated as follows: Group 1, 10% SDS was added to wells A1-A3, B1-B3, and C1-C3; Group 2, 100 μM LL-37 was added to D1-D3; Group 3, untreated induced bacterial cells in wells E1-E3 (control); Group 4, 100 μM LL-37 added to wells F1-F3. Samples were incubated for 15 minutes post-treatment, and 20 μL of 20 mg/mL X-gal substrate was added to each well and allowed to incubate for 15 minutes at 37° C. The colorimetric results are shown in FIG. 4b.

Group 1 cells treated with the lytic agent (SDS) yielded a mild color change, whereas Group 2 cells treated with 100 uM LL-37 completely converted from pink to blue. Untreated Group 3 cells remained pink, and non-induced Group 4 cells were treated with the lytic agent and remained pink, illustrating that the bacteria do not naturally express or produce β-galactosidase unless cultured to do so by an induction method.

Example 2

Transfection of *E. coli*

*E. coli* cells transfected with the lacZ gene that encodes the protein β-galactosidase were obtained. The cells were plated to produce isolate colonies that were then selected.

Example 3

Duplication of *E. coli* Colonies

An isolate colony of lacZ transfected *E. coli* from the plate of Example 2 was looped and inoculated into 10 mL of RPMI 1640 medium+glucose (available from ThermoFisher Scientific, Waltham, Mass.) and incubated at 37° C. for 24 hours.

Example 4

Bacterial Assay

The liquid bacterial culture from Example 3 was removed from incubation and centrifuged at 1200 RPM for 7 minutes. The supernatant was removed, and the bacterial pellet was resuspended in 1 mL of RPMI 1640 (−glucose) liquid tissue culture medium as Sample A. A 15 mL centrifuge tube was filled with induction media (8.9 mL RPMI 1640 (−glucose), 100 μL induced IPTG. 1 mL of the resuspended bacterial culture from Sample A was added to the new tube as Sample B, for a final volume of 10 mL. Sample B was incubated at 37° C. for 60 minutes.

Figure 5A:
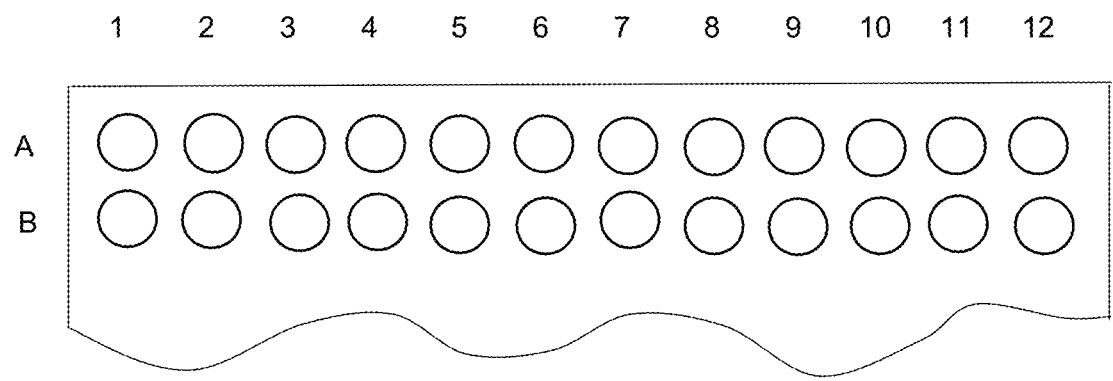
FIG. 5a is a top plan view of a welled plate.

A standard flat bottomed 96-well plate was then obtained, as shown in FIG. 5a. After incubation, 100 μL of Sample B was transferred to each of wells A1-A12 and B1-B12. 10 μL of a 2000 μM LL-37 stock solution was then added to well A1, and a 1:2 dilution was conducted across wells A2-A11. The dilution was repeated for wells B1-B11. No LL-37 solution was added to wells A12 and B12 (controls). The plate was incubated for 15 minutes at room temperature.

20 μL of 5-bromo-4-chloro-3-indoyl-β-D-galactopyranoside (X-gal) substrate (20 mg/mL) was then added to each of wells A1-A12 and B1-B12. X-gal was used to test for the presence of β-galactosidase by producing blue compounds as a result of enzyme-catalyzed hydrolysis. The plate was incubated for 15 minutes at 37° C.

Figure 5B:
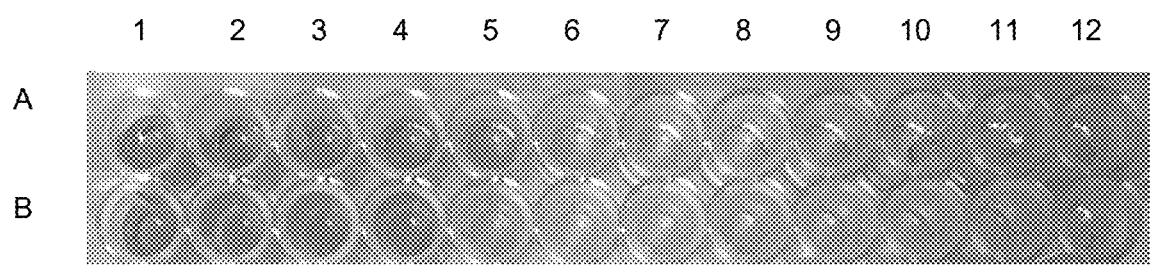
FIG. 5b is a photograph illustrating the plate of FIG. 5a during use.

After incubation, the plate was visually inspected for color change, as shown in FIG. 5b. Particularly, wells that appeared blue (A1-A5 and B1-B5) were the result of the lytic ability of LL-37, which infiltrated the bacterial membrane and led to the release of β-galactosidase. The free β-galactosidase interacted with the free X-gal added to each plate well. Wells that remained pink were the result of bacterial cells in the presence of inactive of LL-37 (wells A6-A11 and B6-B11), or wells that were not treated with LL-37 (wells A12 and B12).

Example 5

Bacterial Assay II

Figure 6A:
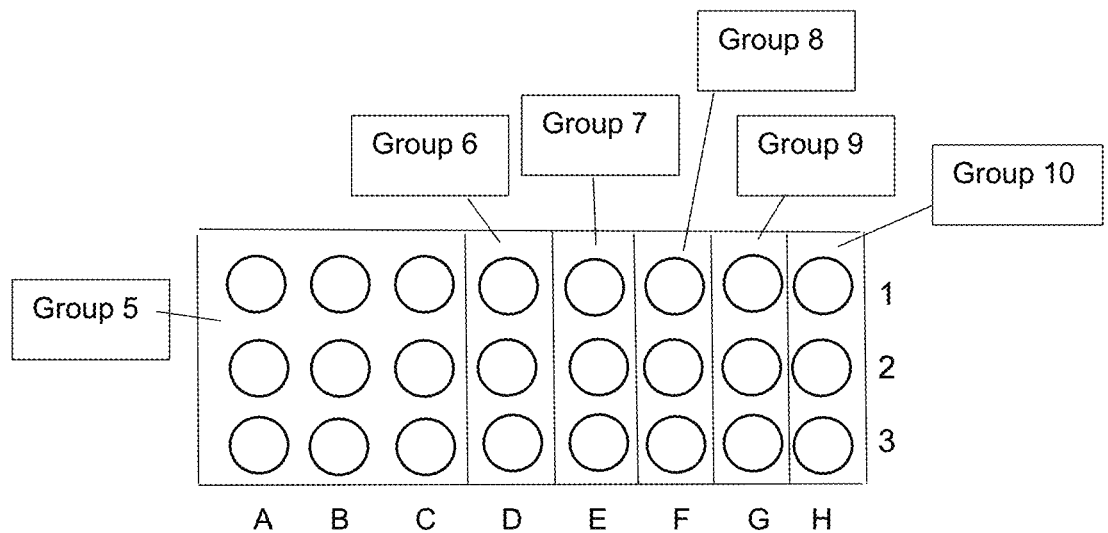
FIG. 6a is a top plan view of a welled plate.

A plate was designed as set forth in FIG. 6a: Group 5, induced bacterial cells treated with 100 uM LL-37 (wells A1-A3, B1-B3, C1-C3); Group 6, induced bacterial cells treated with 10% PBS (wells D1-D3), Group 7, non-induced bacteria treated with a lytic agent (wells E1-E3); Group 8, non-induced bacteria untreated (wells F1-F3); Group 9, induced bacteria treated with a lytic agent (wells G1-G3); and Group 10, untreated induced bacteria.

Figure 6B:
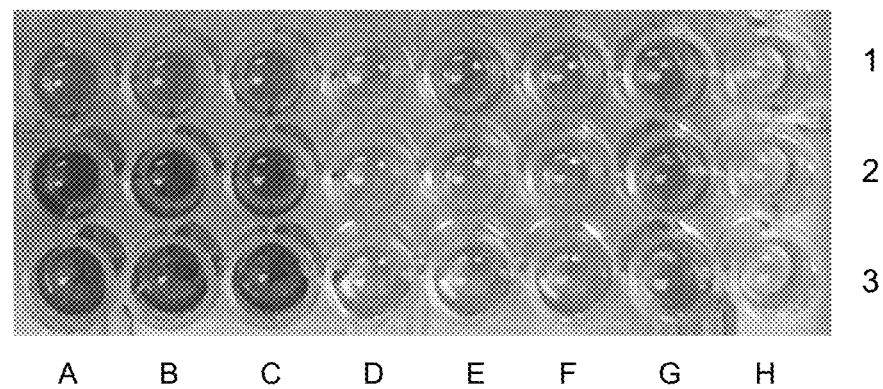
FIG. 6b is a photograph illustrating the plate of FIG. 6a during use.

Samples were incubated for 15 minutes post-treatment, and 20 uL of 20 mg/mL X-gal substrate was added to each well and allowed to incubate for 15 minutes at 37° C. The results are shown in FIG. 6b.

Group 5 cells treated with LL-37 completely converted from pink to blue. Group 6 cells treated with the solvent (PBS) remained pink, indicating that PBS does not possess any lytic capability compared to treatment with LL-37, nor does it influence the lytic ability of the peptide or agent. Group 7 cells treated with the lytic agent yielded a mild color change. Group 8 untreated cells remained pink, and Group 9 non-induced cells treated with the lytic agent and remained pink, illustrating that the bacteria do not naturally express or produce β-galactosidase unless cultured to do so.

Example 6

Bacterial Assay III

Figure 7A:
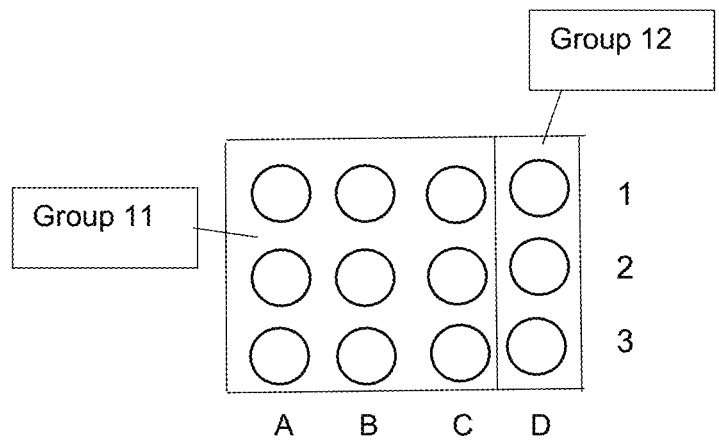
FIG. 7a is a top plan view of a welled plate.
Figure 7B:
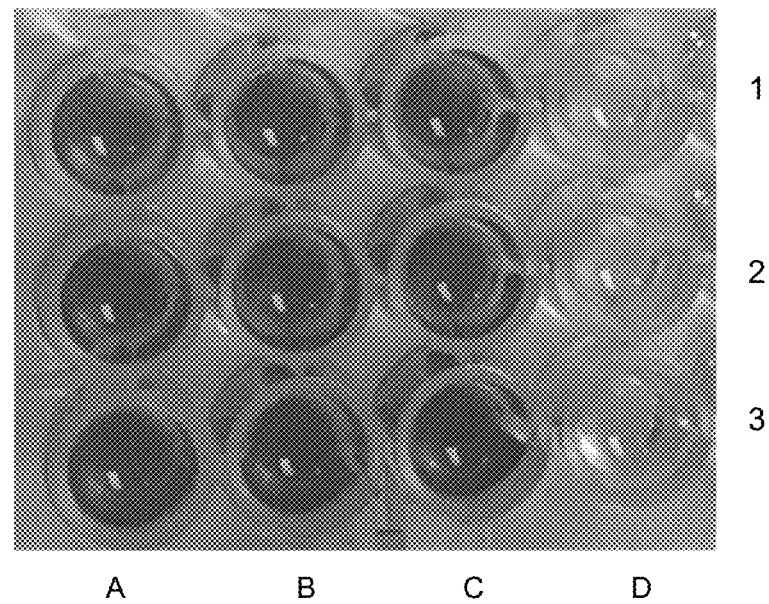
FIG. 7b is a photograph illustrating the plate of FIG. 7a during use.

A plate was designed as set forth in FIG. 7a: Group 11, induced bacteria were treated with 100 uM LL-37 (wells A1-A3, B1-B3, and C1-C3); Group 12, induced bacteria that were untreated (wells D1-D3). Samples were incubated for 15 minutes post-treatment, and 20 uL of 20 mg/mL X-gal substrate was added to each well and allowed to incubate for 15 minutes at 37° C. The results are shown in FIG. 7b.

Cells treated with 100 uM LL-37 completely converted the well color from pink to blue. Untreated cells remained pink, highlighting the lytic capability of LL-37 to permeate the membrane and cause the release of B-galactosidase into the supernatant where it interacts with the added substrate in suspension to yield a blue color.

Example 7

Bacterial Assay IV

Figure 8A:
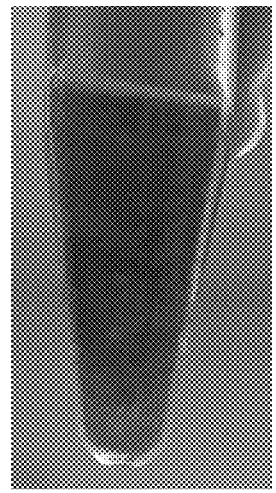
FIGS. 8a-8c are photographs illustrating a color change assay.
Figure 8B:
Figure 8C:
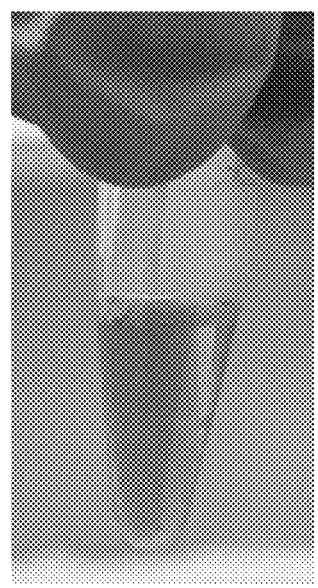

Aliquots of induced bacteria were prepared with 1 mL of the sample dispensed into three Eppendorf tubes. Samples were then lyophilized. After 72 hours to ensure stability, tubes were rehydrated with 1 mL of RPMI 1640 (+) Glucose culture medium and treated. 50 uL of 20 mg/mL X-gal substrate was added to each tube and allowed to incubate for 15 minutes at 37° C. The results are shown in FIGS. 8a-8c.

Samples treated with 100 uM LL-37 (FIGS. 8a and 8b) converted the tube color from pink to blue. Untreated cells (FIG. 8c) remained pink, highlighting the lytic capability of LL-37 to permeate the membrane and cause the release of β-galactosidase into the supernatant where it interacts with the added substrate in suspension to yield a blue color.

What is claimed is:

1. An in vitro method for detecting the presence and activity of a membrane lytic peptide in a sample, the method comprising:
   inducing bacterial cells to express an enzyme by incubating for 1 hour in induction media;
   lyophilizing the bacterial cells;
   contacting the lyophilized bacterial cells with the sample, wherein the sample comprises an amount of the membrane lytic peptide and a substrate that produces a color change in the presence of the enzyme released from the bacterial cells;
   incubating the bacterial cells with the sample for a desired amount of time during which time the enzyme is being released to interact with a colorless substrate;
   detecting the presence and activity of the membrane lytic peptide in the sample by colorimetric analysis, based on lytic action of the membrane lytic peptide on the bacterial cell membrane, creating pores that enable the release of the enzyme;
   wherein the total time from contacting to detecting is 0.5-3.5 hours.

2. The method of claim 1, wherein the membrane lytic peptide is an antimicrobial peptide.

3. The method of claim 1, wherein the membrane lytic peptide is human LL-37.

4. The method of claim 2, wherein the membrane lytic peptide is synthetic LL-37.

5. The method of claim 1, wherein the enzyme is β-galactosidase and the substrate is 5-bromo-4-chloro-3-indolyl-β-d-galactopyranoside.

6. The method of claim 1, wherein the color change comprises a blue color in the presence of the enzyme.

7. The method of claim 1, wherein the lyophilization comprises reducing the temperature of the bacterial cells in incubation media to the triple point.

8. The method of claim 7, wherein the incubating is for 1 hour or less.

9. A method of detecting a chronic condition or disorder in a subject, wherein the chronic condition or disorder is characterized by the presence of an antimicrobial membrane lytic peptide, the method comprising:
   inducing bacterial cells for 1 hour to express an enzyme;
   lyophilizing the bacterial cells;
   obtaining a sample from the subject, wherein the sample is selected from blood, saliva, urine, or combinations thereof;
   contacting the lyophilized bacterial cells with the sample, wherein the sample comprises an amount of the antimicrobial membrane lytic peptide;
   contacting the lyophilized bacterial cells with a substrate that produces a color change in the presence of the enzyme released from the bacterial cells;
   incubating the bacterial cells for a desired amount of time during which time the enzyme is being released to interact with a colorless substrate;
   detecting the presence of the membrane lytic peptide in the sample by colorimetric analysis of the color change in the sample,
   wherein the color change is based on the lytic action of the membrane lytic peptide on the bacterial cell membrane, creating pores that enable the release of the enzyme;
   wherein the presence of the membrane lytic peptide indicates the presence of the chronic condition or disorder in the subject; and
   wherein the total time from contacting the lyophilized bacterial cells with the sample to detecting is 0.5-3.5 hours.

10. The method of claim 9, wherein the antimicrobial membrane lytic peptide is human LL-37.

11. The method of claim 9, wherein the antimicrobial membrane lytic peptide is synthetic LL-37.

12. The method of claim 9, wherein the enzyme is β-galactosidase and the substrate is 5-bromo-4-chloro-3-indolyl-β-d-galactopyranoside.

13. The method of claim 9, wherein the color change comprises a blue color in the presence of the enzyme, indicative of the presence of the chronic condition or disorder in the sample.

14. The method of claim 9, wherein the chronic condition or disorder is selected from one or more of chronic obstructive pulmonary disease (COPD), asthma, psoriasis, systemic lupus erythematosus, and cancer progression.

15. The method of claim 9, wherein the lyophilization comprises reducing the temperature of the bacterial cells in incubation media to the triple point.

16. The method of claim 9, wherein the incubating is for 1 hour or less.

17. The method of claim 1, wherein the incubating is at room temperature.

18. The method of claim 9, wherein the incubating is at room temperature.

19. The method of claim 1, wherein the total time from contacting to detecting is about 0.5-1 hour.

20. The method of claim 9, wherein the total time from contacting to detecting is about 0.5-1 hour.

* * * * *